United States Patent
Li et al.

(10) Patent No.: US 10,422,692 B1
(45) Date of Patent: Sep. 24, 2019

(54) SPECTROMETER DEVICE, MOBILE APPARATUS, SPECTROMETER SYSTEM AND OPERATING METHOD THEREOF

(71) Applicant: InnoSpectra Corporation, Hsinchu County (TW)

(72) Inventors: Hsi-Pin Li, Hsinchu County (TW); Ming-Chih Chen, Hsinchu County (TW); He-Yi Hsieh, Hsinchu County (TW); Ming-Hui Lin, Hsinchu County (TW)

(73) Assignee: InnoSpectra Corporation, Hsinchu County (TW)

( * ) Notice: Subject to any disclaimer, the term of this patent is extended or adjusted under 35 U.S.C. 154(b) by 0 days.

(21) Appl. No.: 16/286,602

(22) Filed: Feb. 27, 2019

(30) Foreign Application Priority Data

Mar. 2, 2018 (CN) .......................... 2018 1 0174084

(51) Int. Cl.
*G01J 3/02* (2006.01)
*G01N 21/25* (2006.01)
*G01J 3/28* (2006.01)

(52) U.S. Cl.
CPC ............. *G01J 3/0264* (2013.01); *G01J 3/027* (2013.01); *G01J 3/0272* (2013.01); *G01J 3/0275* (2013.01); *G01J 3/28* (2013.01); *G01N 21/255* (2013.01); *G01N 2201/0221* (2013.01)

(58) Field of Classification Search
CPC ........ G01J 3/0264; G01J 3/0272; G01J 3/027; G01J 3/0275; G01J 3/28; G01N 2201/0221; G01N 21/255; G08C 17/02; H04M 1/725
See application file for complete search history.

(56) References Cited

U.S. PATENT DOCUMENTS

2008/0266564 A1* 10/2008 Themelis .............. G01J 3/2823
356/419
2017/0160131 A1 6/2017 Goldring et al.

* cited by examiner

*Primary Examiner* — Abdullahi Nur
(74) *Attorney, Agent, or Firm* — JCIPRNET

(57) ABSTRACT

A spectrometer system including a spectrometer device, a mobile apparatus and a cloud server is provided. The spectrometer device scans a target object according to one of a plurality of sets of spectral scan setting parameters to generate spectral data. The mobile apparatus sets the spectrometer device to select one set from the plurality of sets spectral scan setting parameters for scanning the target object. The mobile apparatus receives the spectral data from the spectrometer device and outputs the spectral data. The cloud server stores detection models and the spectral data received from the mobile apparatus, and analyzes the spectral data according to one of the detection models to output an analysis result to the mobile apparatus. The spectrometer system can reduce network transmission traffic and prevent object analysis and model building from being affected by unregulated spectral data so correctness of spectral scan can be controlled.

32 Claims, 7 Drawing Sheets

SPECTROMETER DEVICE, MOBILE APPARATUS, SPECTROMETER SYSTEM AND OPERATING METHOD THEREOF

CROSS-REFERENCE TO RELATED APPLICATION

This application claims the priority benefit of China application serial no. 201810174084.9, filed on Mar. 2, 2018. The entirety of the above-mentioned patent application is hereby incorporated by reference herein and made a part of this specification.

BACKGROUND OF THE INVENTION

1. Field of the Invention

The invention relates to a spectrometer device, a mobile apparatus, a spectrometer system and an operating method thereof.

2. Description of Related Art

Spectrometer is widely used in material analysis applications and can be used together with smart mobile apparatus (laptop, smart phone or tablet computer) as a widely-used sensing device on the Internet of Things through cloud technology. The smart mobile apparatus has a data processor and a wireless communication module, and can receive a spectral signal (spectral data) from the spectrometer and then transmit such signal to a cloud server.

The data transmitted to the cloud server by the smart mobile apparatus are not limited to the spectral data but also include meta data that may offer help in qualitative classification or quantitative estimation, such as non spectral-based data including object's name, type, size, temperature, location, time, spectrometer serial number, user identity, etc., or spectral-based data including spectral correction parameter, spectrometer scan parameter, light source parameter, etc. However, in the current use situation, the meta data and the spectral data are simultaneously transmitted to the cloud server. In reality, the received meta data in the cloud server is repetitive, and thus problems of unnecessary consumption for network transmission traffic and transmission delay may arise due to the repeatedly transmitted meta data. Further, under certain situations, because the meta data transmitted by user are not regulated data, which may affect object analysis or model building and makes it unable to control correctness and consistency in the spectral scan.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the invention were acknowledged by a person of ordinary skill in the art.

SUMMARY OF THE INVENTION

The invention provides a spectrometer device, a mobile apparatus, a spectrometer system and an operating method thereof, which are capable of saving both network transmission traffic and storage space of the cloud server, and preventing object analysis and model building from being affected by unregulated spectral data so correctness and consistency of spectral scan can be effectively controlled.

Other objects and advantages of the invention can be further illustrated by the technical features broadly embodied and described as follows.

To achieve one, a part, or all of the objects or other objects, a spectrometer system is provided according to an embodiment of the invention. The spectrometer system includes a spectrometer device, a mobile apparatus and a cloud server. The spectrometer device scans a target object according to one set of spectral scan setting parameters among a plurality of sets of spectral scan setting parameters to generate spectral data. The mobile apparatus sets the spectrometer device to select one set of spectral scan setting parameters from the plurality of sets of spectral scan setting parameters for scanning the target object. The mobile apparatus receives the spectral data from the spectrometer device and outputs the spectral data. The cloud server stores detection models and the spectral data received from the mobile apparatus, and analyzes the spectral data according to one of the detection models to output an analysis result to the mobile apparatus.

To achieve one, a part, or all of the objects or other objects, a spectrometer device is provided according to another embodiment of the invention. The spectrometer device includes a spectrometer engine, which scans a target object according to one set of spectral scan setting parameters among a plurality of sets of spectral scan setting parameters to generate spectral data. The spectrometer engine outputs the spectral data to the mobile apparatus.

To achieve one, a part, or all of the objects or other objects, a mobile apparatus is provided according to another embodiment of the invention. The mobile apparatus sets the spectrometer device to select one set of spectral scan setting parameters from a plurality of sets of spectral scan setting parameters for scanning a target object to generate spectral data. The mobile apparatus receives the spectral data from the spectrometer device.

To achieve one, a part, or all of the objects or other objects, an operating method of a spectrometer system is provided according to another embodiment of the invention. The spectrometer system includes a spectrometer device, a mobile apparatus and a cloud server. The operating method includes: setting the spectrometer device to operate in a default mode; in the default mode, selecting one detection model from a plurality of detection models for controlling the spectrometer device to scan a target object according to one set of spectral scan setting parameters corresponding to the selected detection model among the plurality of sets of spectral scan setting parameters to generate spectral data; transmitting the spectral data from the spectrometer device to the cloud server through the mobile apparatus; and analyzing the spectral data according to the detection model so as to output an analysis result to the mobile apparatus.

To achieve one, a part, or all of the objects or other objects, an operating method of a spectrometer system is provided according to another embodiment of the invention. The spectrometer system includes a spectrometer device, a mobile apparatus and a cloud server. The operating method includes: setting the spectrometer device to operate in an expert mode; setting a detection model in the expert mode; controlling the spectrometer device to scan at least one modeling object according to a default set of spectral scan setting parameters to correspondingly generate at least one spectral data; and transmitting said at least one spectral data from the spectrometer device to the cloud server through the mobile apparatus; completing the step of building the detection model.

Based on the above, the embodiments of the invention have at least one of the following advantages and effects. In the exemplary embodiments of the invention, the spectrometer system may have the spectrometer device scanning the target object for the spectral data according to one set of spectral scan setting parameters, and may have the mobile apparatus receiving the spectral data and transmitting the spectral data to the cloud server for generating the analysis result to be transmitted to the mobile apparatus. In this way, not only can both network transmission traffic and storage space of the cloud server be saved, object analysis and model building can also be prevented from being affected by unregulated data so correctness and consistency of spectral scan can be effectively controlled.

Other objectives, features and advantages of the present invention will be further understood from the further technological features disclosed by the embodiments of the present invention wherein there are shown and described preferred embodiments of this invention, simply by way of illustration of modes best suited to carry out the invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

It is to be understood that other embodiment may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

In the following embodiments, a signal processor or a controller related to a spectrometer engine, at least one processor of a mobile apparatus and at least one processor of a cloud server may be, for example, a central processing unit (CPU), or other programmable devices for general purpose or special purpose, such as a microprocessor and a digital signal processor (DSP), a programmable controller, an application specific integrated circuit (ASIC), a programmable logic device (PLD) or other similar devices or a combination of those circuits or chips. A display screen of the mobile apparatus may be, for example but not limited to, a liquid crystal display (LCD) or an organic light-emitting diode (OLED) display panel. A storage area of the spectrometer engine, a storage device of the mobile apparatus and a storage device of the cloud server may be, for example, a portable random access memory (RAM), a read-only memory (ROM), a flash memory or similar devices or a combination of the aforementioned devices. A wireless communication interface and a wired communication of the mobile apparatus or a network interface of the cloud server are defined as media capable of conducting data exchange, which include but not limited to, for example, circuits, chips or interfaces adopting Bluetooth, Wi-Fi, wireless personal area network (Zigbee) or other wireless transmission technologies, or other wired circuit, chips or interfaces adopting optical fiber, mobile High-Definition Link (MHL), cable line, etc.

Figure 1:
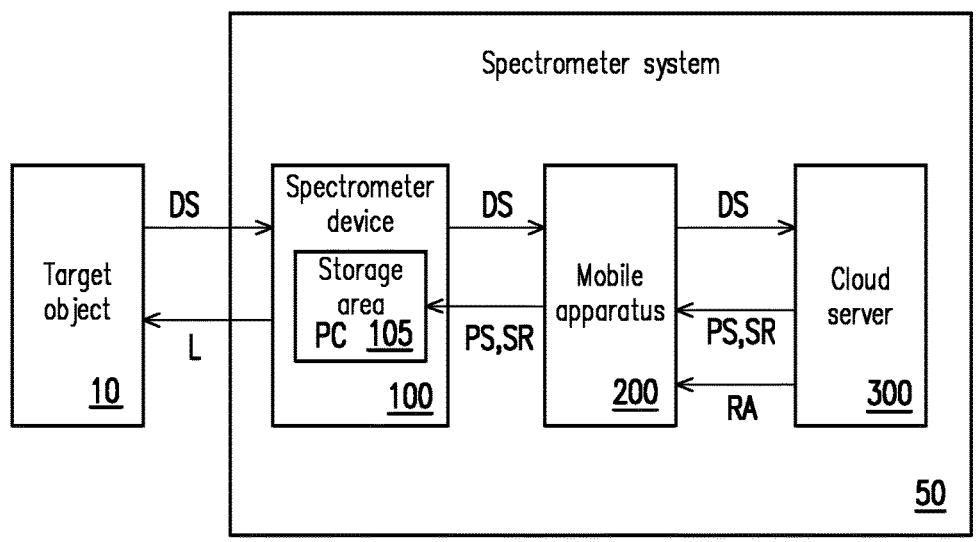
FIG. 1 illustrates a system block diagram of a spectrometer system according to an embodiment of the invention.
Figure 2:
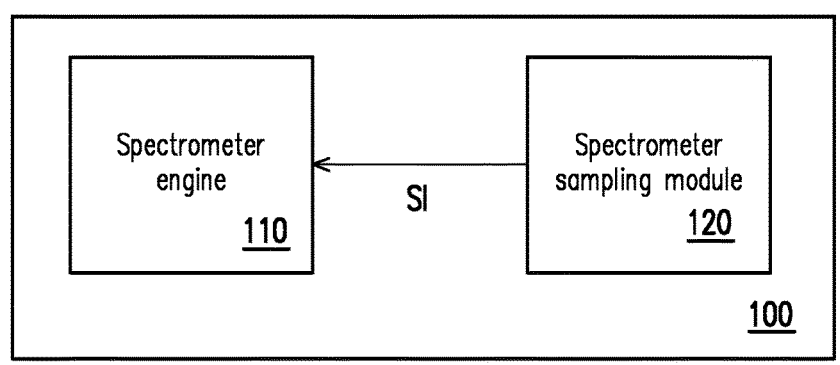
FIG. 2 is a device block diagram of the spectrometer device illustrated in FIG. 1.

FIG. 1 illustrates a system block diagram of a spectrometer system according to an embodiment of the invention. FIG. 2 is a device block diagram of the spectrometer device illustrated in FIG. 1. With reference to FIG. 1 and FIG. 2, in this embodiment, a spectrometer system 50 includes a spectrometer device 100, a mobile apparatus 200 and a cloud server 300. The spectrometer device 100 includes a spectrometer engine 110 and a spectrometer sampling module 120, and the spectrometer engine 110 is electrically connected to the spectrometer sampling module 120. The spectrometer engine 110 of this embodiment is at least composed of elements like a slit module, a grating device, a wavelength selector, a photo detector, a signal processor, a controller and a memory. However, type and structure of the spectrometer engine 110 are not particularly limited by the invention.

The spectrometer engine 110 of this embodiment may be paired with said spectrometer sampling module 120 of at least three types to form the spectrometer device 100. For instance, the spectrometer sampling module 120 may be a transmissive module, a reflective module or an optical fiber module, but the invention is not limited thereto. Accordingly, the spectrometer engine 110 may determine a type of the paired spectrometer sampling module 120 according to an identification signal SI of the spectrometer sampling module 120, and then select a corresponding calibration parameter PC stored in a storage area 105 (the memory) so that the spectrometer device 100 can calibrate an object light DS1 obtained by scanning according to the calibration parameter PC to provide accurate measurement quality. Here, the storage area 105 is disposed in the spectrometer engine 110.

The mobile apparatus 200 of this embodiment at least includes a processor, a storage device, a display screen, a wireless communication interface and a wired communication interface. Here, the mobile apparatus may be a laptop computer, a smart phone or a tablet computer.

The cloud server 300 of this embodiment at least includes one processor, one storage device and one network interface, and the storage device of the cloud server 300 may be used to store analysis software and models to be processed by the processor. Further, the storage device of the cloud server 300 may be used as a database, and may also store spectral data DS transmitted through the mobile apparatus 200.

In terms of operation, the spectrometer device 100 may scan a target object 10 according to one set of spectral scan setting parameters PS among a plurality of sets of spectral scan setting parameters PS to generate an object light DS1. Here, each set of spectral scan setting parameters PS among the plurality of sets of spectral scan setting parameters PS corresponds to a reference signal SR. In detail, the spectrometer device 100 emits a scan light L onto the target object 10 so the object light DS1 is generated by the target object 10. The spectrometer device 100 receives the object light DS1 to be converted into the spectral data DS corresponding to the object light DS1. In addition, the storage area 105 of the spectrometer device 100 in this embodiment may store the plurality of sets of spectral scan setting parameters PS and the corresponding reference signals SR. Here, each corresponding set of spectral scan setting parameters PS and the reference signal SR may correspond to at least one spectrum analysis model, and the spectrometer device 100 may correspondingly scan the target object 10 according to different spectral detection models. It is worth noting that, persons skilled in the art can easily learn that the reference signal SR may be reset through operations of the mobile apparatus 200 or the cloud server 300 according to the spectral data obtained by scanning a white sample (reference sample) by manufacturers or user using the spectrometer device 100. The new reference signal SR may also be re-transmitted (updated) to the spectrometer device 100 or stored in the mobile apparatus 200 or the cloud server 300. In this case, the one set of spectral scan setting parameters PS will correspond to the new reference signal SR.

The mobile apparatus 200 is configured to set the spectrometer device 100 to select one set of spectral scan setting parameters PS from the plurality of sets of spectral scan setting parameters PS for scanning the target object 10. In other words, the spectrometer engine 110 may drive the spectrometer sampling module 120 according to a control signal from the mobile apparatus 200 to select one set of spectral scan setting parameters PS in cooperation with the target object 10 for scanning the target object 10 to generate the object light DS1. Upon scanning, the mobile apparatus 200 may receive the scanned target object 10 from the spectrometer device 100 to be processed by the spectrometer engine 110 in order to obtain the spectral data DS, and may then output this spectral data DS to the cloud server 300.

The cloud server 300 is configured to receive the spectral data DS transmitted from the mobile apparatus 200, and analyze the spectral data DS according to detection models in the cloud server 300. The cloud server 300 is used to output an analysis result RA to the mobile apparatus 200. However, the invention is not limited to the above. The analysis result RA may also be stored in the storage device in the cloud server 300. In this embodiment, the meta data refers to not only data related to the spectral data DS but also data that may offer help in qualitative classification or quantitative estimation for the spectrometer device 100, such as non spectral-based data including object's name, type, size, temperature, location, time, spectrometer serial number, user identity, etc., but the invention is not limited to the above. Finally, the mobile apparatus 200 displays the analysis result RA on the display screen of the mobile apparatus 200 so that user can obtain related information corresponding to the target object 10. The related information is, for example, variety, origin, composition, sweetness of the target object, and even growth time course of the object.

For instance, in this embodiment, the spectrometer system 50 may use one suitable spectrum analysis model according to different types of the target object 10, so as to scan the target object 10 according to the corresponding set of spectral scan setting parameters PS and the corresponding reference signal SR. Table 1 below lists the plurality of sets of spectral scan setting parameters PS corresponding to the different types of the target object 10 that may be included by the spectrometer system 50, but the invention is not limited thereto. The spectral scan setting parameters include wavelength range, spectrum sampling points, exposure/integration time, average number of scans and light source intensity. An user can choice several abovementioned spectral scan setting parameters to be a set of spectral scan setting parameters.

TABLE 1

| Scan parameter configuration | Cotton materials | Medicines | Fruit (Apple) | Fruits (Mango) | Fruit (Date) |
| --- | --- | --- | --- | --- | --- |
| Wavelength range | 1100~1900 nm | 1100~1650 nm | 950~1650 nm | 950~1650 nm | 950~1650 nm |
| Spectrum sampling points | 128 | 256 | 128 | 128 | 128 |
| Exposure/ integration time | 5 ms | 10 ms | 5 ms | 5 ms | 2 ms |
| Average number of scans | 10 | 10 | 15 | 15 | 20 |
| Light source intensity | 100% | 90% | 95% | 95% | 90% |

It is worth noting that, in this embodiment, the one set of spectral scan setting parameters PS and the reference signal SR may be stored in the spectrometer device 100, the mobile apparatus 200 or the cloud server 300 or stored in two or more different devices described above, which are not particularly limited by the invention. In this way, the transmission traffic for the plurality of sets of spectral scan setting parameters PS and the reference signal SR may be reduced so as to improve operating and processing speed for the spectrometer system 50.

Figure 3:
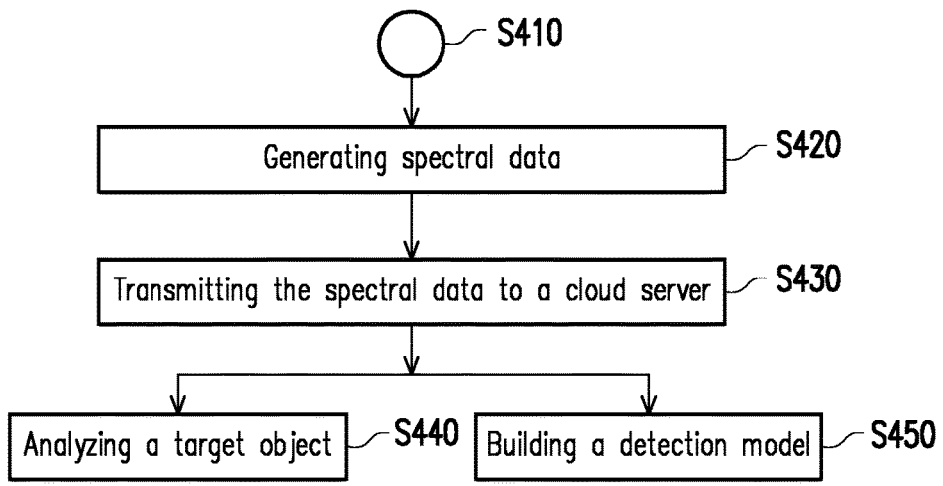
FIG. 3 illustrates a flowchart for analyzing target object and building detection model according to an embodiment of the invention.

FIG. 3 illustrates a flowchart for analyzing target object and building detection model according to an embodiment of the invention. Referring to FIG. 1 and FIG. 3 together, in this embodiment, the mobile apparatus 200 may have the spectrometer device 100 capturing the object light DS1 of the target object 10 so the spectrometer device 100 may generate the spectral data DS and transmit the spectral data DS to the cloud server 300 for analyzing the spectral data DS or building the detection model. In step S410, the spectrometer device 100 is activated to select corresponding one set of the plurality of sets of spectral scan setting parameters PS and the reference signal SR according to the target object 10 to be scanned. Then, in step S420, the spectrometer device 100 emits the scan light L on the target object 10 according to the selected set of plurality of sets of spectral scan setting parameters PS and the reference signal SR to capture the object light DS1 of the target object 10, so as to generate the spectral data DS. Then, in step S430, the spectral data DS is transmitted to the cloud server 300. Specifically, the spectrometer device 100 will transmit the spectral data DS to the mobile apparatus 200, and the mobile apparatus 200 will transmit the spectral data DS the cloud server 300 for analyzing the target object 10 in step S440 or building the detection model in step S450. In detail, in step 440, the cloud server 300 analyzes the received spectral data DS and then outputs the analysis result RA to the mobile apparatus 200 so as to complete analyzing the target object 10. In step S450, user may further use the received spectral data DS to build the detection model in a specific mode.

The mobile apparatus 200 has a display interaction which refers to, for example, an operating interface provided by an application in the mobile apparatus 200 and displayed on the display screen. In this embodiment, the display interaction of the mobile apparatus includes options of a default mode and an expert mode, and the mobile apparatus 200 may control operations of the spectrometer device 100 according to a user command in either the default mode or the expert mode. For instance, when the mobile apparatus 200 is, for example, a smart phone with touch functions, the user command is, for example, a touch signal provided by user to the smart phone, but the invention is not limited thereto.

Figure 4:
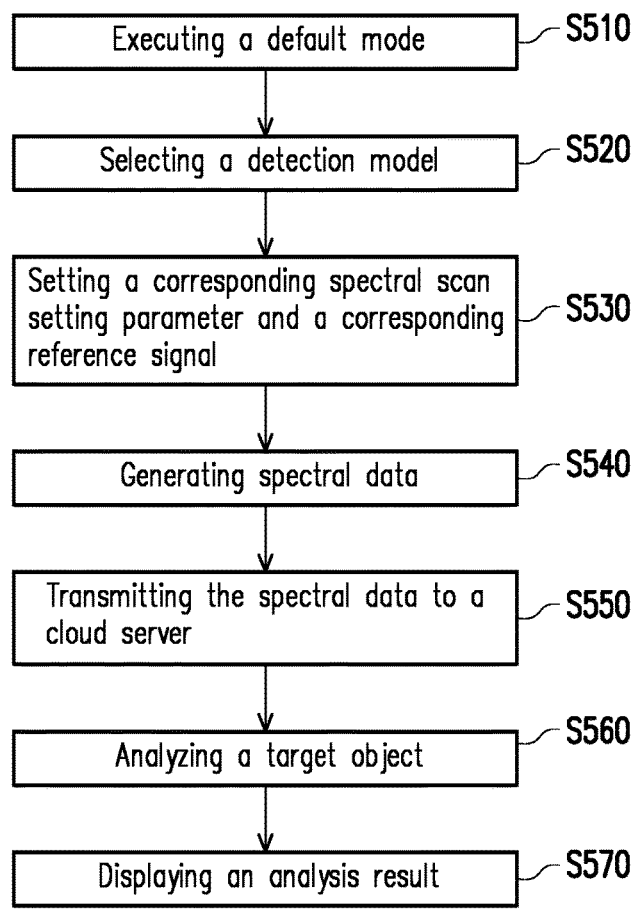
FIG. 4 illustrates a flowchart for operating with a default mode according to an embodiment of the invention.

FIG. 4 illustrates a flowchart for operating with a default mode according to an embodiment of the invention. Referring to FIG. 1 and FIG. 4 together, steps in the process of operating with the default mode may at least be applied in the spectrometer system 50 illustrated in FIG. 1, but the invention is not limited thereto. In this embodiment, the mobile apparatus 200 controls operations of the spectrometer device 100. In the default mode, the mobile apparatus 200 selects one detection model from a plurality of detection models and the mobile apparatus 200 sets the spectrometer device 100 to scan the target object 10 according to one set of spectral scan setting parameters PS corresponding to the selected detection model among the plurality of sets of spectral scan setting parameters PS.

Specifically, in step S510, the default mode is executed. Then, in step S520, the detection model is selected. For instance, if the target object 10 is a cotton material, user may directly select the detection model for detecting cotton materials. Then, in step S530, the one set of spectral scan setting parameters PS corresponding to the selected detection model and the corresponding reference signal SR are set. Then, in step S540, the spectral data DS is generated. Then, in step S550, the spectral data DS is transmitted to the cloud server 300. In step S560, the target object 10 is analyzed. Lastly, in step S570, the analysis result RA is displayed.

Figure 5:
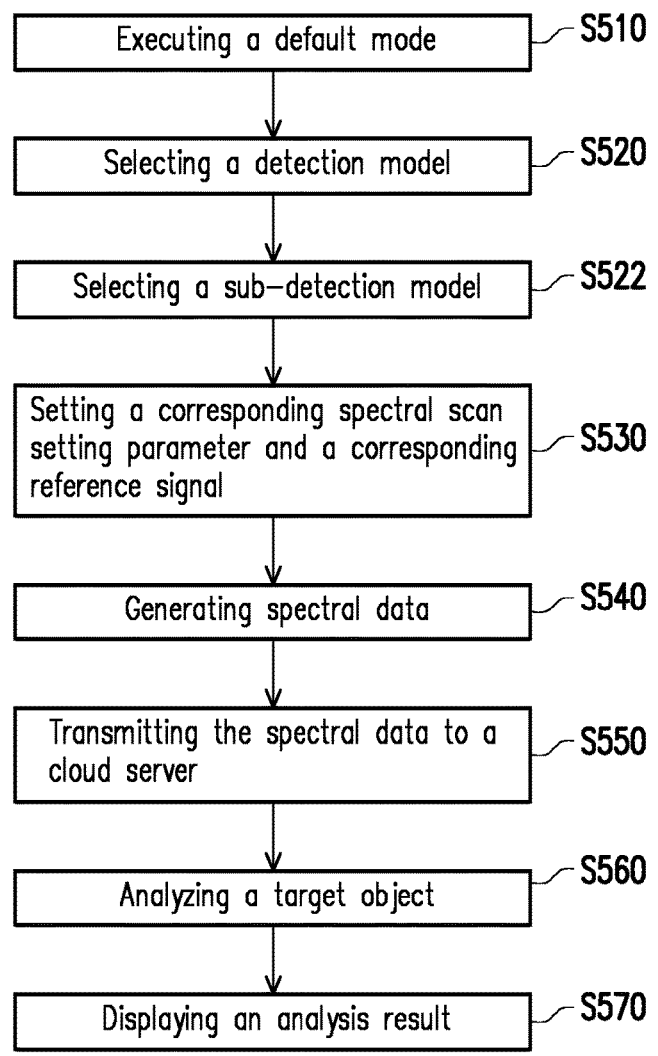
FIG. 5 illustrates a flowchart for operating with a default mode according to another embodiment of the invention.

FIG. 5 illustrates a flowchart for operating with a default mode according to an embodiment of the invention. Referring to FIG. 1 and FIG. 5 together, steps in the process of operating with the default mode may at least be applied in the spectrometer system 50 illustrated in FIG. 1, but the invention is not limited thereto. Steps in process of operating with the default mode in this embodiment are similar to steps in process of operating with the default mode in the embodiment of FIG. 4, and the difference between the two is described as follows. In this embodiment, the selected detection model includes a plurality of sub-detection models, the mobile apparatus 200 selects one sub-detection model from the sub-detection models, and the mobile apparatus 200 sets the spectrometer device to scan the target object 10 according to one set of spectral scan setting parameters corresponding to the selected sub-detection model among the plurality of sets of spectral scan setting parameters PS.

Specifically, after step S520, step S522 is performed to select the sub-detection model. For instance, if the target object 10 is a specific fruit (e.g., an apple), user may select the detection model for detecting fruits in step S520, and then selects the sub-detection model corresponding to the specific fruit for scanning thereby generating the spectral data DS in step S522. In this way, accuracy of the spectroscopic analysis may be further improved.

Figure 6:
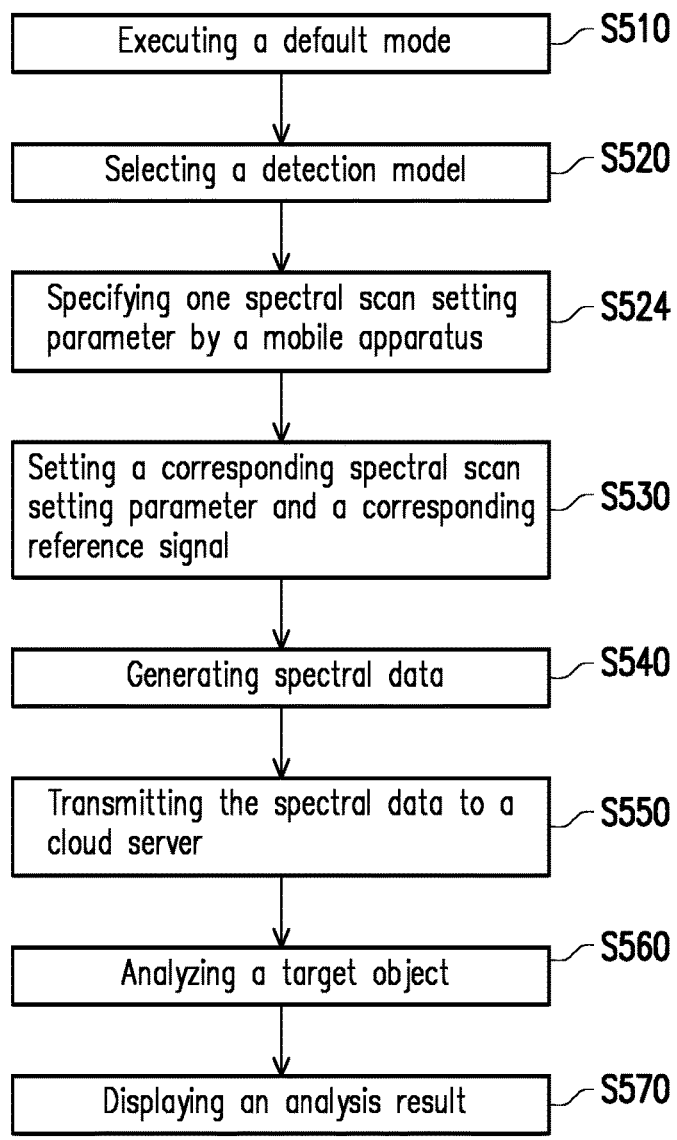
FIG. 6 illustrates a flowchart for operating with a default mode according to another embodiment of the invention.

FIG. 6 illustrates a flowchart for operating with a default mode according to an embodiment of the invention. Referring to FIG. 1 and FIG. 6 together, steps in the process of operating with the default mode may at least be applied in the spectrometer system 50 illustrated in FIG. 1, but the invention is not limited thereto. Steps in process of operating with the default mode in this embodiment are similar to steps in process of operating with the default mode in the embodiment of FIG. 4, and the difference between the two is described as follows. In this embodiment, after step S520, step S524 is performed such that the mobile apparatus 200 specifies one set of spectral scan setting parameters PS. In detail, the so-called "the mobile apparatus 200 specifies . . . " is defined as follows. After the detection model is selected by user, the mobile apparatus 200 will notify the spectrometer device 100 that it is required to select one set of spectral scan setting parameters PS stored in the spectrometer device 100, or the mobile apparatus 200 provides one set of spectral scan setting parameters PS to be transmitted to the spectrometer device 100. It is worth noting that, in other embodiments, the mobile apparatus 200 can notify the spectrometer device 100 and provide one new set of spectral scan setting parameters PS to the spectrometer device 100. According to such one set of spectral scan setting parameters PS and a built-in reference signal SR, the spectrometer device 100 then resets a new reference signal SR corresponding to such one set of spectral scan setting parameters PS, which can be used to update the set of spectral scan setting parameters PS and the reference signal SR in the spectrometer device 100.

Figure 7:
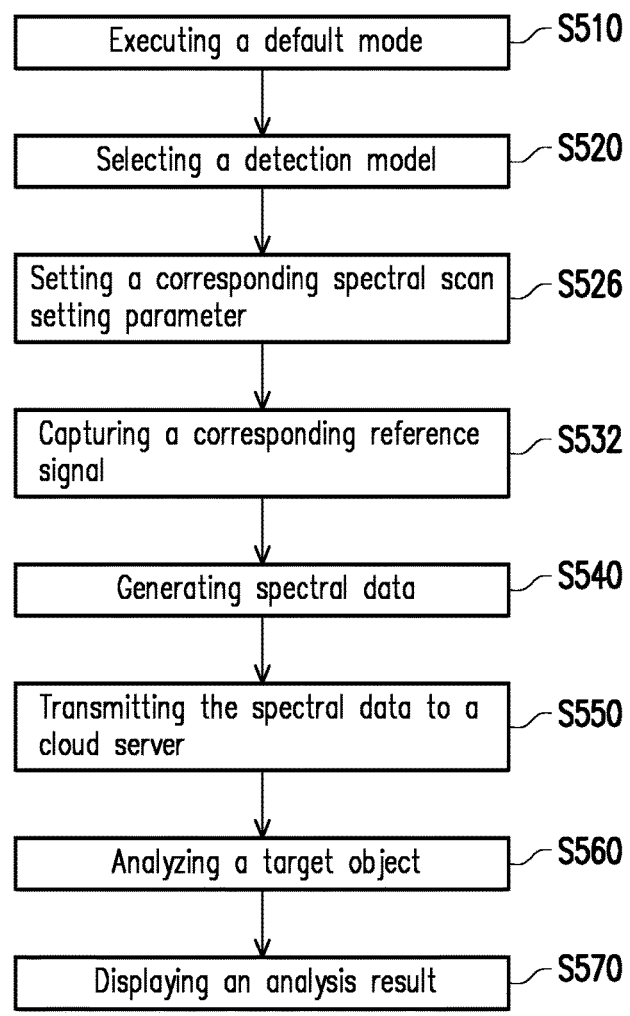
FIG. 7 illustrates a flowchart for operating with a default mode according to another embodiment of the invention.

FIG. 7 illustrates a flowchart for operating with a default mode according to an embodiment of the invention. Referring to FIG. 1 and FIG. 7 together, steps in the process of operating with the default mode may at least be applied in the spectrometer system 50 illustrated in FIG. 1, but the invention is not limited thereto. Steps in process of operating with the default mode in this embodiment are similar to steps in process of operating with the default mode in the embodiment of FIG. 4, and the difference between the two is described as follows. In this embodiment, after step S520, step S526 is performed such that the corresponding one set of spectral scan setting parameters PS is set. Then, step S532 is performed such that the corresponding reference signal SR is captured. In other words, after the detection model is selected by user, a default value built in the spectrometer device 100 may be selected as the reference signal SR, or the spectrometer device 100 may send the command to the mobile apparatus 200 so the corresponding reference signal SR may be captured by ways of re-scanning the object (i.e., the step of updating the reference signal SR).

Figure 8:
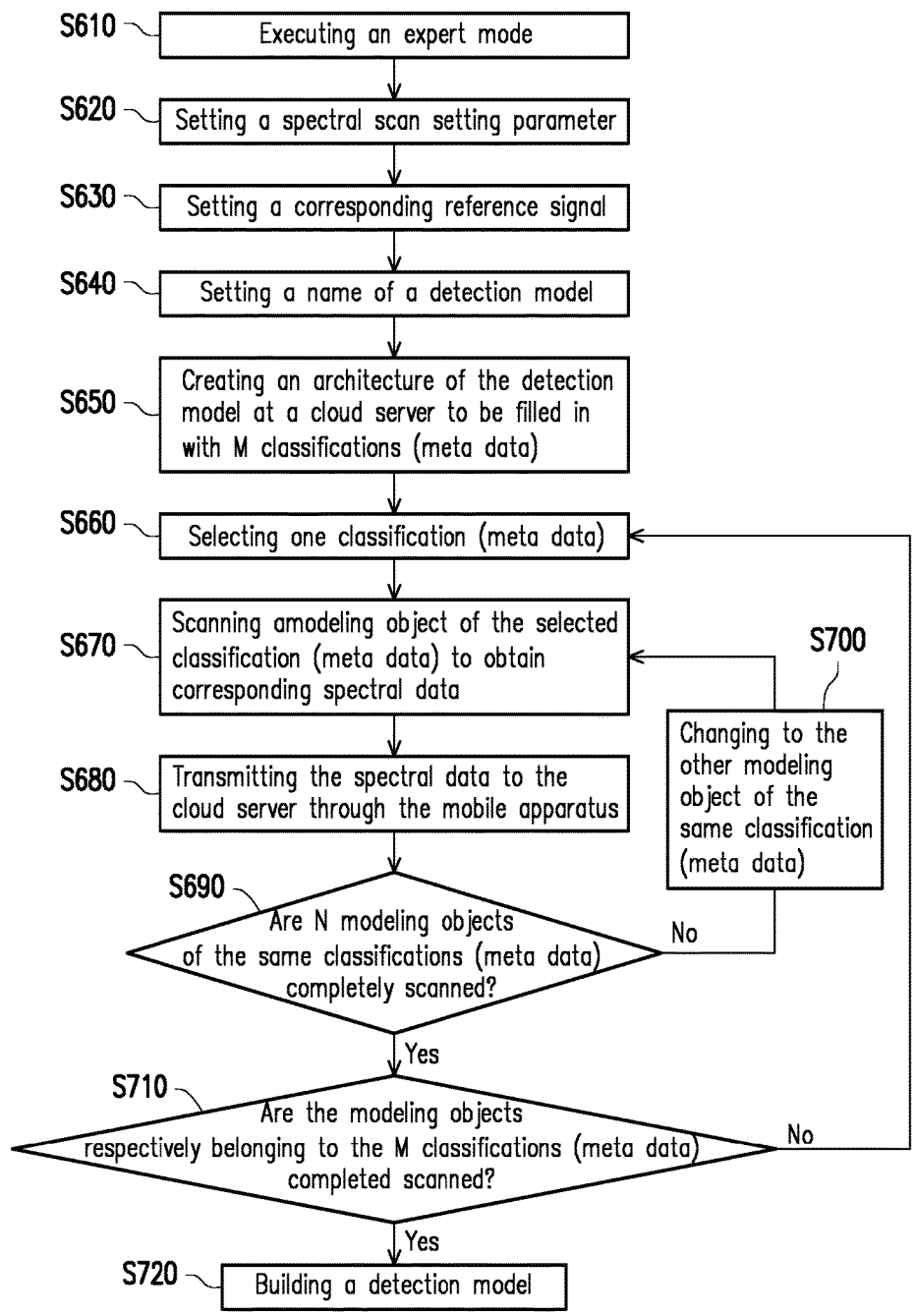
FIG. 8 illustrates a flowchart for operating with an expert mode according to an embodiment of the invention.

FIG. 8 illustrates a flowchart for operating with an expert mode according to an embodiment of the invention. Referring to FIG. 1 and FIG. 8 together, steps in the process of operating with the expert mode may at least be applied in the spectrometer system 50 illustrated in FIG. 1, but the invention is not limited thereto. In this embodiment, the mobile apparatus 200 controls the spectrometer device 100 to operate in the expert mode. In the expert mode, a pre-built detection model may be set by the mobile apparatus 200. Then, the spectrometer device 100 is controlled by the mobile apparatus 200 to scan at least one modeling object according to one set of spectral scan setting parameters PS so as to correspondingly generate at least one spectral data. In this process, the one set of spectral scan setting parameters PS may be created in advance in the mobile apparatus 200 or the cloud server 300 or preset in the spectrometer device 100, and the invention is not limited thereto. Then, the mobile apparatus 200 receives the spectral data DS and outputs the spectral data DS to the cloud server 300 so as to complete building the detection model.

Specifically, in step S610, the expert mode is executed in the mobile apparatus 200. Then, in step S620, the one set of spectral scan setting parameters PS is set. Then, in step S630, the corresponding reference signal SR is set. Then, in step S640, a name of the detection model is set at the cloud server 300 through operations of the mobile apparatus 200. However, the invention is not limited to the above. The name may also be directly set by the cloud server 300. Accordingly, user can build the detection model on his/her own and can restrict or grant access for other users based on demand (e.g., an access right may be restricted by account name and password). Then, in step S650, an architecture of the detection model is created at the cloud server 300 and filled in with M classifications (meta data), wherein M is a positive integer adjustable according to the actual change in a number of classifications. For instance, user can create the detection model for medicines in this step, and further set a plurality of meta data according to different types of medicines so as to form a plurality of different classifications under the architecture of the detection model. Then, in step S660, one classification is selected. Then, in step S670, the corresponding spectral data DS is obtained by the spectrometer device 100 by scanning the modeling object of the selected classification and transmitted to the mobile apparatus 200. Then, in step S680, the spectral data DS is transmitted to the cloud server 300 through the mobile apparatus 200. Afterwards, in step S690, either step S700 or step S710 is to be executed may be determined according to whether N modeling objects of the same classifications (meta data) are completely scanned, where N is a positive integer. In an embodiment, a detection module being built has higher accuracy if a value of N is greater. In a preferred embodiment, N is, for example, a positive integer greater than 3, but the invention is not limited thereto. If there are less than N modeling objects being scanned, step S700 is executed for changing to the modeling object belonging to the same classification (meta data), and step S670 and step S680 are repeated in sequence. For instance, user may sequentially change to scan multiple medicines of the same kind to increase overall amount of the spectral data DS so as to improve accuracy for the medicines. In other words, user may continue to scan other modeling objects to obtain more spectral data DS so as to improve accuracy for the detection model. If there are N modeling objects being scanned, step S710 is then executed. In step S710, either step S660 or step S670 is to be executed may be determined according to whether the modeling objects respectively belonging to the M classifications (meta data) are completed scanned. If the modeling objects of the M classifications are not completely scanned, step S660, step S670, step S680 and step S690 are repeatedly executed until the modeling objects of the M classifications are completely scanned. If the modeling objects of the M classifications are completely scanned, step S720 is executed to build the detection model so as to complete the detection module for this kind of object.

After that, user may build the detection model in the expert mode. Also, after the detection model is created, user may use that detection model according to the process of operating with the default mode described above. In other words, user is not required to repeatedly upload the meta data of the model building to the cloud server 300 but simply transmits only the spectral data DS of the modeling object. In this way, not only can both network transmission traffic and a storage capacity of the cloud server be saved, object analysis and model building can also be prevented from being affected by unregulated data so correctness and consistency of spectral scan can be effectively controlled.

Figure 9:
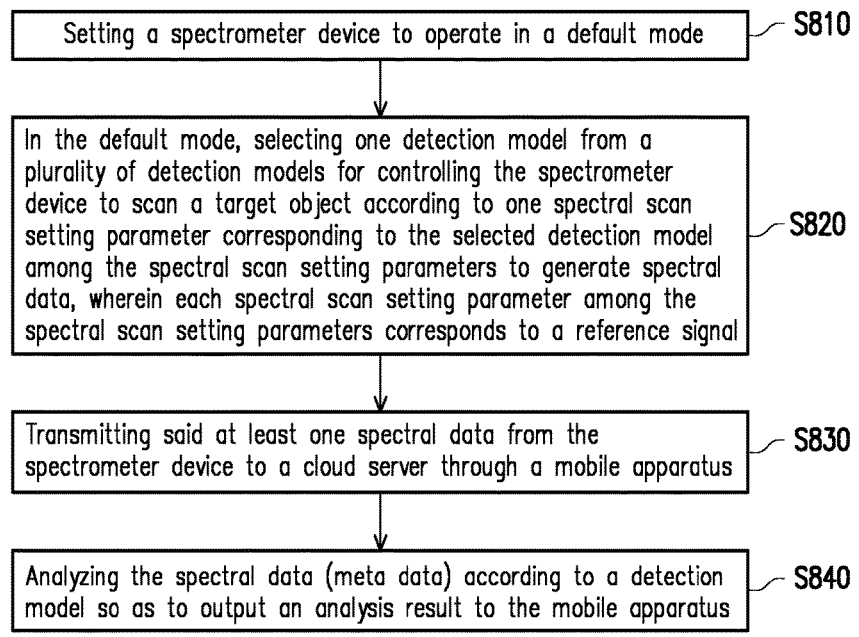
FIG. 9 illustrates a flowchart of an operating method of a spectrometer system according to an embodiment of the invention.

FIG. 9 illustrates a flowchart of an operating method of a spectrometer system according to an embodiment of the invention. With reference to FIG. 9, steps in the process of operating with the default mode may at least be applied in the spectrometer system 50 illustrated in FIG. 1. User can execute the operating method of this embodiment to operate the spectrometer system, but the invention is not limited thereto. In step S810, the spectrometer device is set to operate in the default mode. Then, in step S820, in the default mode, selecting one detection model from a plurality of detection models and controlling the spectrometer device to scan a target object according to one set of spectral scan setting parameters corresponding to the selected detection model among the plurality of sets of spectral scan setting parameters to generate spectral data, wherein each set of spectral scan setting parameters among the plurality of sets of spectral scan setting parameters corresponds to a reference signal. In step S830, said at least one spectral data is transmitted from the spectrometer device to the cloud server through the mobile apparatus; In step S840, the spectral data (meta data) is analyzed according to the detection model so as to output an analysis result to the mobile apparatus.

In other embodiments, said operating method further includes selecting one sub-detection model from a plurality of sub-detection models and controlling the spectrometer device to scan the target object according to one set of spectral scan setting parameters corresponding to the selected sub-detection model among the plurality of sets of spectral scan setting parameters to generate the spectral data.

Figure 10:
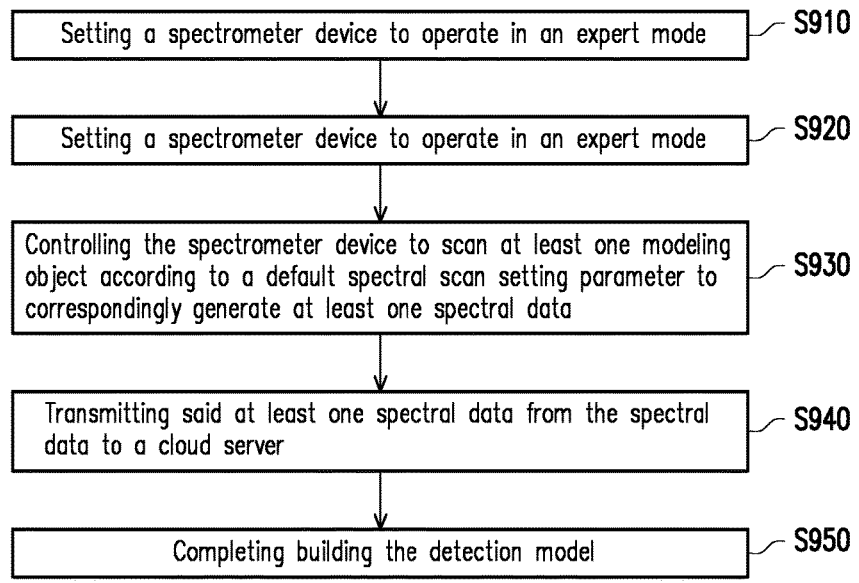
FIG. 10 illustrates a flowchart of an operating method of a spectrometer system according to another embodiment of the invention.

FIG. 10 illustrates a flowchart of an operating method of a spectrometer system according to another embodiment of the invention. With reference to FIG. 10, steps in the process of operating with the expert mode may at least be applied in the spectrometer system 50 illustrated in FIG. 1. User can execute the operating method of this embodiment to operate the spectrometer system, but the invention is not limited thereto. In step S910, the spectrometer device is set to operate in the expert mode. Then, in step S920, a detection model is set in the expert mode. Then, in step S930, the spectrometer device is controlled to scan at least one modeling object according to a default set of spectral scan setting parameters to correspondingly generate at least one spectral data. In step S940, said at least one spectral data is transmitted from the spectral data to the cloud server. Lastly, in step S950, completing building the detection model.

In other embodiments, after step S920, step of creating at least one classification in the detection model and step of providing multiple groups of said at least one modeling object according to said at least one modeling object are further included. In addition, after step S930, step of completing creating said at least one classification is further included. In other words, user may continue to scan the modeling objects of the same classification based on demand to obtain the spectral data in order to improve accuracy of such classification, and may also scan the modeling objects of other classifications to obtain the spectral data in order to improve integrity of the detection module. However, the disclosure is not limited to the above.

In summary, the embodiments of the invention have at least one of the following advantages and effects. In the exemplary embodiments of the invention, the spectrometer system may have the spectrometer device scanning the target object for the spectral data according to one set of spectral scan setting parameters and the corresponding reference signal, and may have the mobile apparatus receiving the spectral data and transmitting the spectral data to the cloud server for generating the analysis result to be transmitted to the mobile apparatus. In this way, not only can both network transmission traffic and storage space of the cloud server be saved, object analysis and model building can also be prevented from being affected by unregulated data so correctness and consistency of spectral scan can be effectively controlled.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A spectrometer system, comprising a spectrometer device, a mobile apparatus and a cloud server,
   the spectrometer device being configured to scan a target object according to one set of spectral scan setting parameters among a plurality of sets of spectral scan setting parameters to generate spectral data;
   the mobile apparatus being configured to set the spectrometer device to select the one set of spectral scan setting parameters from the plurality of sets of spectral scan setting parameters for scanning the target object, wherein the mobile apparatus receives the spectral data from the spectrometer device and outputs the spectral data;
   the cloud server being configured to store a plurality of detection models and the spectral data received from the mobile apparatus, and analyze the spectral data according to one of the detection models so as to output an analysis result to the mobile apparatus.

2. The spectrometer system according to claim 1, wherein the plurality of sets of spectral scan setting parameters are stored in a storage device of the spectrometer device, the mobile apparatus or the cloud server.

3. The spectrometer system according to claim 1, wherein a display interaction of the mobile apparatus comprises a default mode and an expert mode, and the mobile apparatus controls the spectrometer device to operate in the default mode or the expert mode according to a user command.

4. The spectrometer system according to claim 1, wherein the mobile apparatus controls the spectrometer device to operate in the default mode, and in the default mode, the mobile apparatus selects one detection model from the detection models according to a user command and sets the spectrometer device to scan the target object according to the one set of spectral scan setting parameters corresponding to the selected detection model among the plurality of sets of spectral scan setting parameters.

5. The spectrometer system according to claim 4, wherein the selected detection model comprises a plurality of sub-detection models, and the mobile apparatus selects one sub-detection model from the sub-detection models according to the user command and sets the spectrometer device to scan the target object according to the one set of spectral scan setting parameters corresponding to the selected sub-detection model among the plurality of sets of spectral scan setting parameters.

6. The spectrometer system according to claim 1, wherein the mobile apparatus controls the spectrometer device to operate in the expert mode, and in the expert mode, the mobile apparatus controls the spectrometer device to scan at least one modeling object to correspondingly generate at least one spectral data, receives the at least one spectral data and outputs the at least one spectral data to the cloud server so as to build new detection models or update the detection models.

7. The spectrometer system according to claim 6, wherein in the expert mode, the spectrometer device scans the target object according to the one set of spectral scan setting parameters corresponding to the at least one modeling object.

8. The spectrometer system according to claim 1, wherein each set of spectral scan setting parameters among the plurality of sets of spectral scan setting parameters corresponds to a reference signal.

9. The spectrometer system according to claim 1, wherein a reference signal is stored in a storage device of the spectrometer device, the mobile apparatus or the cloud server.

10. A spectrometer device, comprising:
a spectrometer engine, scanning a target object according to one set of spectral scan setting parameters among a plurality of sets of spectral scan setting parameters to generate spectral data, wherein the spectrometer engine outputs the spectral data to a mobile apparatus.

11. The spectrometer device according to claim 10, wherein the plurality of sets of spectral scan setting parameters are stored in a storage device of the spectrometer device, the mobile apparatus or a cloud server.

12. The spectrometer device according to claim 10, wherein the spectrometer engine operates in a default mode, and in the default mode, the spectrometer engine is operative to select one detection model from a plurality of detection models and scan the target object according to one set of spectral scan setting parameters corresponding to the selected detection model among the plurality of sets of spectral scan setting parameters.

13. The spectrometer device according to claim 12, wherein the selected detection model comprises a plurality of sub-detection models, and the spectrometer engine is operative to select one sub-detection model from the sub-detection models and scan the target object according to one set of spectral scan setting parameters corresponding to the selected sub-detection model among the plurality of sets of spectral scan setting parameters and a corresponding reference signal value.

14. The spectrometer device according to claim 10, wherein the spectrometer engine operates in an expert mode, and in the expert mode, the spectrometer engine scans at least one modeling object to generate at least one corresponding spectral data and outputs the at least one spectral data to a cloud server through the mobile apparatus so as to build new detection models or update the detection models.

15. The spectrometer device according to claim 10, wherein a cloud server receives the spectral data from the mobile apparatus, and analyzes the spectral data according to a detection model so as to output an analysis result to the mobile apparatus.

16. The spectrometer device according to claim 10, further comprising a spectrometer sampling module, the spectrometer engine being electrically connected to the spectrometer sampling module, wherein the spectrometer engine determines a type of the paired spectrometer sampling module according to an identification signal of the spectrometer sampling module.

17. The spectrometer device according to claim 10, wherein each set of spectral scan setting parameters among the plurality of sets of spectral scan setting parameters corresponds to a reference signal.

18. The spectrometer device according to claim 10, wherein a reference signal is stored in a storage device of the spectrometer device, the mobile apparatus or a cloud server.

19. A mobile apparatus for controlling operations of a spectrometer device, wherein the mobile apparatus sets the spectrometer device to select one set of spectral scan setting parameters from a plurality of sets of spectral scan setting parameters for scanning a target object to generate spectral data, wherein the mobile apparatus receives the spectral data from the spectrometer device.

20. The mobile apparatus according to claim 19, wherein the plurality of sets of spectral scan setting parameters are stored in a storage device of the spectrometer device, the mobile apparatus or a cloud server.

21. The mobile apparatus according to claim 19, wherein a display interaction of the mobile apparatus comprises a default mode and an expert mode, and the mobile apparatus controls the spectrometer device to operate in the default mode or the expert mode according to a user command.

22. The mobile apparatus according to claim 19, wherein the mobile apparatus controls the spectrometer device to operate in the default mode, and in the default mode, the mobile apparatus selects one detection model from a plurality of detection models according to a user command and sets the spectrometer device to scan the target object according to one set of spectral scan setting parameters corresponding to the selected detection model among the plurality of sets of spectral scan setting parameters.

23. The mobile apparatus according to claim 22, wherein the selected detection model comprises a plurality of sub-detection models, and the mobile apparatus selects one sub-detection model from the sub-detection models according to the user command and sets the spectrometer device to scan the target object according to one set of spectral scan setting parameters corresponding to the selected sub-detection model among the plurality of sets of spectral scan setting parameters.

24. The mobile apparatus according to claim 19, wherein the mobile apparatus controls the spectrometer device to operate in the expert mode, and in the expert mode, the mobile apparatus controls the spectrometer device to scan at least one modeling object to generate at least one spectral data, receives the at least one spectral data and outputs the at least one spectral data to a cloud server so as to build new detection models or update the detection models.

25. The mobile apparatus according to claim 19, wherein each set of spectral scan setting parameters among the plurality of sets of spectral scan setting parameters corresponds to a reference signal.

26. The mobile apparatus according to claim 19, wherein a reference signal is stored in a storage device of the spectrometer device, the mobile apparatus or a cloud server.

27. An operating method of a spectrometer system, wherein the spectrometer system comprises a spectrometer device, a mobile apparatus and a cloud server, and the operating method comprises:
setting the spectrometer device to operate in a default mode;
in the default mode, selecting one detection model from a plurality of detection models for controlling the spectrometer device to scan a target object according to one set of spectral scan setting parameters corresponding to the selected detection model among a plurality of sets of spectral scan setting parameters to generate spectral data;
transmitting the spectral data from the spectrometer device to the cloud server through the mobile apparatus; and
analyzing the spectral data according to the detection model so as to output an analysis result to the mobile apparatus.

28. The operating method of the spectrometer system according to claim 27, wherein the selected detection model comprises a plurality of sub-detection models, and the operating method further comprises:
selecting one sub-detection model from the sub-detection models for controlling the spectrometer device to scan the target object according to one set of spectral scan setting parameters corresponding to the selected sub-detection model among the plurality of sets of spectral scan setting parameters to generate the spectral data.

29. An operating method of a spectrometer system, wherein the spectrometer system comprises a spectrometer device, a mobile apparatus and a cloud server, and the operating method comprises:
   setting the spectrometer device to operate in an expert mode;
   setting a detection model in the expert mode;
   controlling the spectrometer device to scan at least one modeling object according to a default set of spectral scan setting parameters to generate at least one spectral data; and
   transmitting the at least one spectral data from the spectrometer device to the cloud server through the mobile apparatus;
   completing the step of building the detection model.

30. The operating method of the spectrometer system according to claim 29, wherein the at least one modeling object is plural, and the step of scanning the at least one modeling object to correspondingly generate the at least one spectral data is repeatedly executed according to a number of the at least one modeling object.

31. The operating method of the spectrometer system according to claim 29, further comprising:
   creating at least one classification in the detection model;
   providing corresponding multiple groups of the at least one modeling object according to the at least one classification; and
   completing the step of creating the detection model.

32. The operating method of the spectrometer system according to claim 31, wherein the at least one classification is plural, and the step of scanning the at least one modeling object to correspondingly generate the at least one spectral data and the step of transmitting the at least one spectral data from the spectrometer device to the cloud server through the mobile apparatus are repeatedly executed according to a number of the at least one classification.

* * * * *